United States Patent [19]
Ritger

[11] Patent Number: 6,008,429
[45] Date of Patent: Dec. 28, 1999

[54] WOUND DRESSING DELIVERY SYSTEM

[76] Inventor: Philip L. Ritger, 5821 Raphael Dr., Huntington Beach, Calif. 92649

[21] Appl. No.: 08/870,478

[22] Filed: Jun. 6, 1997

[51] Int. Cl.⁶ ................................................. A61F 13/00
[52] U.S. Cl. ............................. 602/57; 602/43; 602/57; 602/58; 206/441
[58] Field of Search ..................... 602/41–59; 206/440, 206/441; 604/180

[56] References Cited

U.S. PATENT DOCUMENTS

| | | |
|---|---|---|
| 2,924,331 | 10/1960 | Hoey . |
| 2,969,057 | 11/1961 | Simmons . |
| 3,349,765 | 10/1967 | Blanford . |
| 4,160,328 | 7/1979 | Cartmell et al. . |
| 4,324,237 | 4/1982 | Buttaravoli . |
| 4,485,809 | 12/1984 | Dellas . |
| 4,545,371 | 10/1985 | Grossman et al. . |
| 4,570,627 | 2/1986 | MacConkey et al. . |
| 4,600,001 | 7/1986 | Gilman . |
| 4,646,731 | 3/1987 | Brower . |
| 4,650,705 | 3/1987 | Ghodsian . |
| 4,744,355 | 5/1988 | Faasse, Jr. . |
| 4,747,401 | 5/1988 | Potter et al. . |
| 4,753,323 | 6/1988 | Ward . |
| 4,807,613 | 2/1989 | Koehnke et al. . |
| 4,815,457 | 3/1989 | Mazars et al. . |
| 4,837,062 | 6/1989 | Dunshee et al. . |
| 4,884,563 | 12/1989 | Sessions . |
| 4,909,244 | 3/1990 | Quarfoot et al. . |
| 4,915,102 | 4/1990 | Kwiateck et al. . |
| 4,917,112 | 4/1990 | Kalt . |
| 4,926,850 | 5/1990 | Lott et al. . |
| 4,928,680 | 5/1990 | Sandbank . |
| 5,000,172 | 3/1991 | Ward . |
| 5,018,515 | 5/1991 | Gilman . |
| 5,035,687 | 7/1991 | Sandbank . |
| 5,042,466 | 8/1991 | McKnight . |
| 5,074,293 | 12/1991 | Lott et al. . |
| 5,088,483 | 2/1992 | Heinecke . |
| 5,092,323 | 3/1992 | Riedel et al. . |
| 5,099,832 | 3/1992 | Ward . |
| 5,106,629 | 4/1992 | Cartmell et al. . |
| 5,158,555 | 10/1992 | Porzilli . |
| 5,160,315 | 11/1992 | Heinecke et al. . |
| 5,167,613 | 12/1992 | Karami et al. . |
| 5,204,110 | 4/1993 | Cartmell et al. . |
| 5,255,199 | 10/1993 | Hidaka et al. . |
| 5,336,162 | 8/1994 | Ota et al. . |
| 5,415,627 | 5/1995 | Rasmussen et al. . |
| 5,437,622 | 8/1995 | Carion . |
| 5,489,262 | 2/1996 | Cartmell et al. . |
| 5,628,724 | 5/1997 | DeBusk et al. ............... 602/58 |
| 5,709,651 | 1/1998 | Ward ............................. 602/57 |

FOREIGN PATENT DOCUMENTS

| | | |
|---|---|---|
| 1192825 | 9/1985 | Canada . |
| 0 066 899 A2 | 11/1982 | European Pat. Off. . |
| 0 161 865 A3 | 12/1985 | European Pat. Off. . |
| 0 189 999 A3 | 12/1987 | European Pat. Off. . |
| 0 401 949 A2 | 12/1990 | European Pat. Off. . |
| 38 09 539 A1 | 10/1989 | Germany . |
| 192 792 | 7/1987 | United Kingdom . |

OTHER PUBLICATIONS

Berktek Intergrated Pouch/Patch Delivery Systems, Occlusive HMVT Wound Drassings, Ulcer Dressings, IV Site Dressings FasTape® 1827 S Built–in fingerlift design, single–coated, Transparent Polyurethane Tape, Avery, Sep. 11, 1992.

"Wound Healing Biochemical & Clinical Aspects," W.B. Saunders Company, Harcourt Brace Jovanovich, Inc, 1992.

*Primary Examiner*—Richard J. Apley
*Assistant Examiner*—Kim M. Lee
*Attorney, Agent, or Firm*—Knobbe, Martens, Olson & Bear, LLP

[57] ABSTRACT

Disclosed herein is a three layered wound dressing delivery system comprising a release layer, and adhesive layer, and a protective layer. The release layer is provided with a cut separating the release layer into two portions. A hinge strip is adhered to the protective layer and release layer along at least one of the lateral edges of their lateral edges.

13 Claims, 5 Drawing Sheets

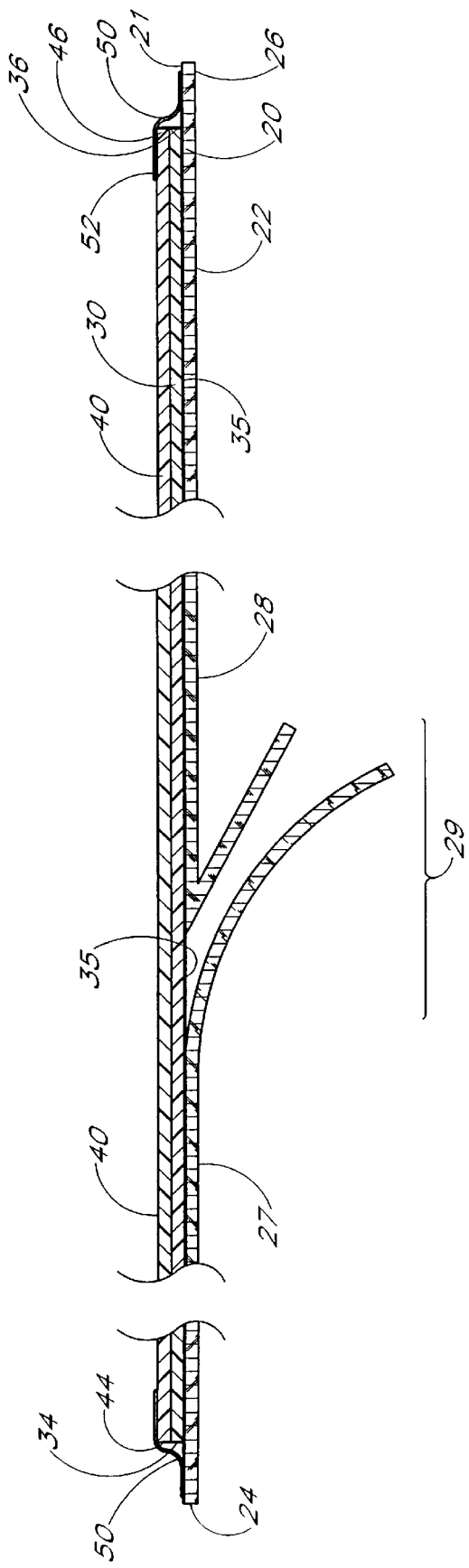

WOUND DRESSING DELIVERY SYSTEM

BACKGROUND OF THE INVENTION

The present invention relates to wound dressings and, in particular, to an improved wound dressing delivery system.

Polymeric wound care dressings are very generally thin "plastic" films with an adherent side that may be applied to a patient. They are commonly used by clinicians in association with managing wounds that occur during or result from various surgical procedures. For example, prior to many surgical procedures, a polymeric wound dressing is applied to the skin of the patient over the site of the operation. Surgical incisions are made through the thin polymeric dressing and into the skin of the patient. The wound dressing permits easier handling of the skin surrounding the incision site and, as a result, increases the accuracy of the incision. Furthermore, use of a wound dressing in this manner reduces the risk of any infection resulting from the surgical procedure.

In other applications, polymeric wound dressings are applied to the patient after the surgery is completed. In these applications, the wound dressings serve the important function of preventing post-operative infection.

Polymeric films useful as wound dressings are known to those of skill in the art. For example, such polymeric films are disclosed in U.S. Pat. No. 5,437,622 to Carion, and U.S. Pat. No. 4,884,563 to Sessions. Both the Carion and Sessions patents disclose in conjunction with the wound dressings various dressing application systems with a number of different nonadherent tabs or strips to assist the clinician in placing the sticky wound dressing to the patient. These strips and tabs result in a more complex structure which increases manufacturing costs. Moreover, the tabs or strips are only helpful in placing a whole wound dressing. Oftentimes, a clinician must cut a wound dressing prior to application to size it to the wound. The placement tabs or strips of the prior art are often ineffective in facilitating application when the dressing must be cut, because the cut portions do not have appropriately placed nonadherent portions that the clinician may grasp when placing the cut dressing.

Accordingly, there exists a need for a wound dressing application system which provides the clinician with improved flexibility in cutting the dressing to size prior to its application, and, at the same time, is of a simple structure to promote low cost manufacturing.

SUMMARY OF THE INVENTION

The present invention provides an improved wound care dressing application system with a design that provides a nonadherent surface for grasping, without the need for added tabs or strips. Consequently, the design is relatively simple, and therefore easier to manufacture, saving the clinician and patient money. As an added benefit, the design permits cutting to a variety of smaller sizes, without impacting the dressing's nonadherent sites for grasping.

In one aspect of the present invention, there is provided a wound dressing application system. The dressing system has a release layer having a first lateral edge and a second lateral edge, the layer having a cut extending across the layer to form a first portion and a second portion. An adhesive layer is releasably adhered to an upper surface of the release layer, the adhesive layer having a first lateral edge and a second lateral edge. The second lateral edge of the adhered adhesive layer terminates prior to the second lateral edge of the release layer such that a portion of the release layer upper surface is exposed.

A protective layer is disposed over a nonadherent surface of the adhesive layer. The protective layer has a first lateral edge and a second lateral edge. The second lateral edge of the protective layer substantially coterminates with the second lateral edge of the adhesive layer.

A strip is adhered to the protective layer along its second lateral edge and to the exposed upper surface of the release layer, to form a hinge.

In one preferred embodiment, the cut comprises a butterfly cut in the release liner. In this an other embodiments, a nonadherent strip may be adhered to the adhesive layer along the first lateral edge of the adhesive layer. A protective layer strip may also be adhered to an upper surface of the protective layer along the first lateral edge of the protective layer.

In another aspect of the present invention, there is provided a wound dressing system which consists of a first layer having a cut dividing it into a first portion and a second portion. A second layer is releasably adhered to the first layer. The second layer is adapted to be peeled from the first layer and adhered to a patient. A third layer is disposed over the second layer, and a strip is adhered to the first and third layers to attach the first layer to the third layer.

In another aspect of the present invention, there is provided a method of applying a tacky wound dressing to a patient, comprising the steps of:

(a) providing a wound dressing system comprising a release layer having a first lateral edge and a second lateral edge, the layer having a cut extending across the layer to form a first portion and a second portion, and an adhesive layer releasably adhered to an upper surface of the release layer, the adhesive layer having a first lateral edge and a second lateral edge, wherein the second lateral edge of the adhered adhesive layer terminates prior to the second lateral edge of the release layer such that a portion of the release layer upper surface is exposed, and a protective layer disposed over a nonadherent surface of the adhesive layer, the protective layer having a first lateral edge and a second lateral edge, wherein the second lateral edge of the protective layer substantially coterminates with the second lateral edge of the adhesive layer, and a strip adhered to the protective layer along its second lateral edge and to the release layer, thereby forming a hinge;

(b) peeling at least the first or second portion of the release sheet adjacent to the cut away from the adhesive layer to expose an adhesive surface of the adhesive layer;

(c) applying the adhesive surface of the adhesive layer to a patient to adhere the adhesive layer to the patient; and (d) removing the protective sheet from the adhesive layer.

BRIEF DESCRIPTION OF THE DRAWINGS

FIG. 5 is a longitudinal cross-sectional view of an alternative embodiment of the present invention featuring hinged lateral edges on opposite ends of the dressing system.

DETAILED DESCRIPTION OF THE PREFERRED EMBODIMENT

Figure 1:
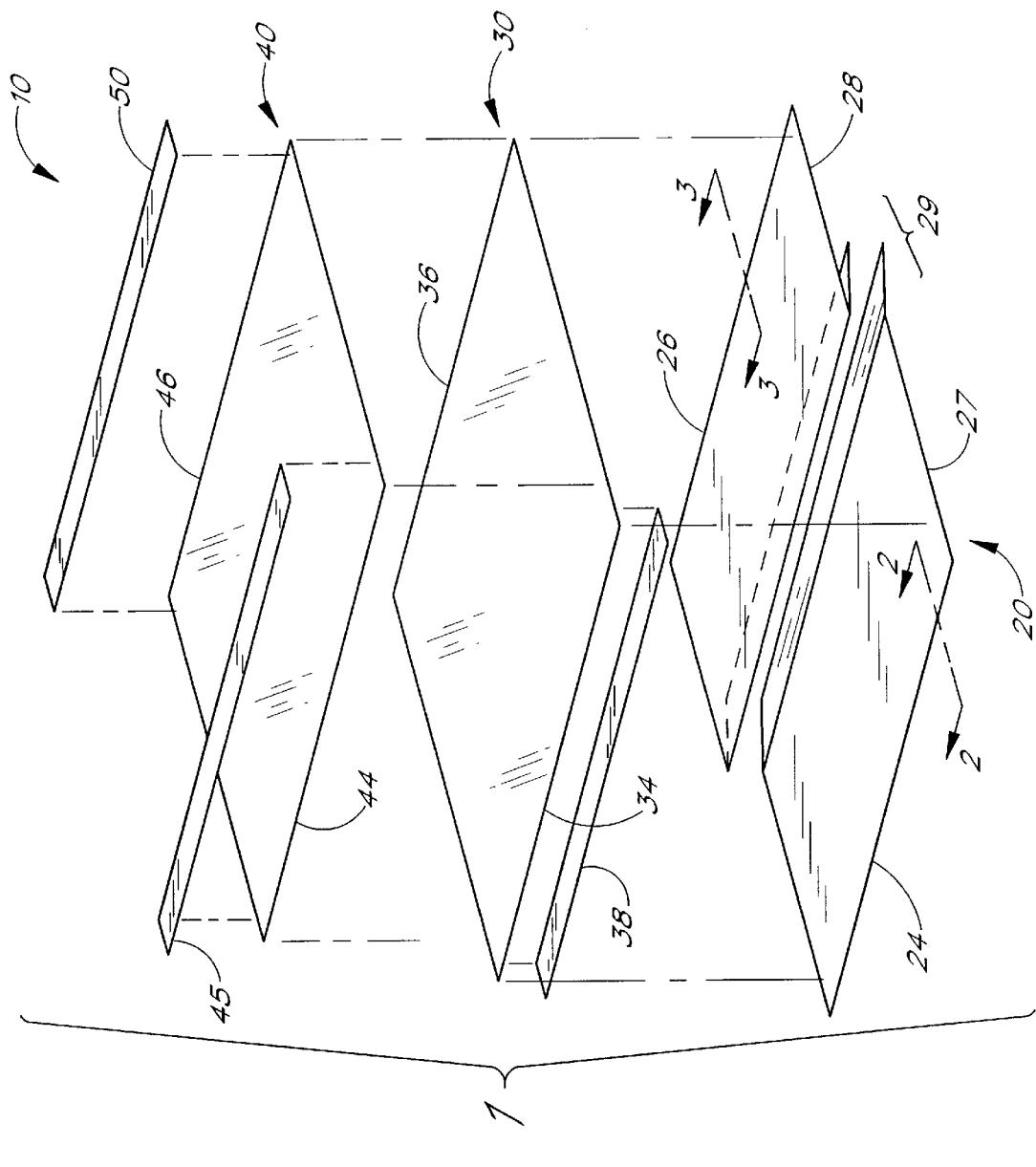
FIG. 1 is an exploded perspective view of an embodiment of wound care dressing of the present invention.
Figure 2:
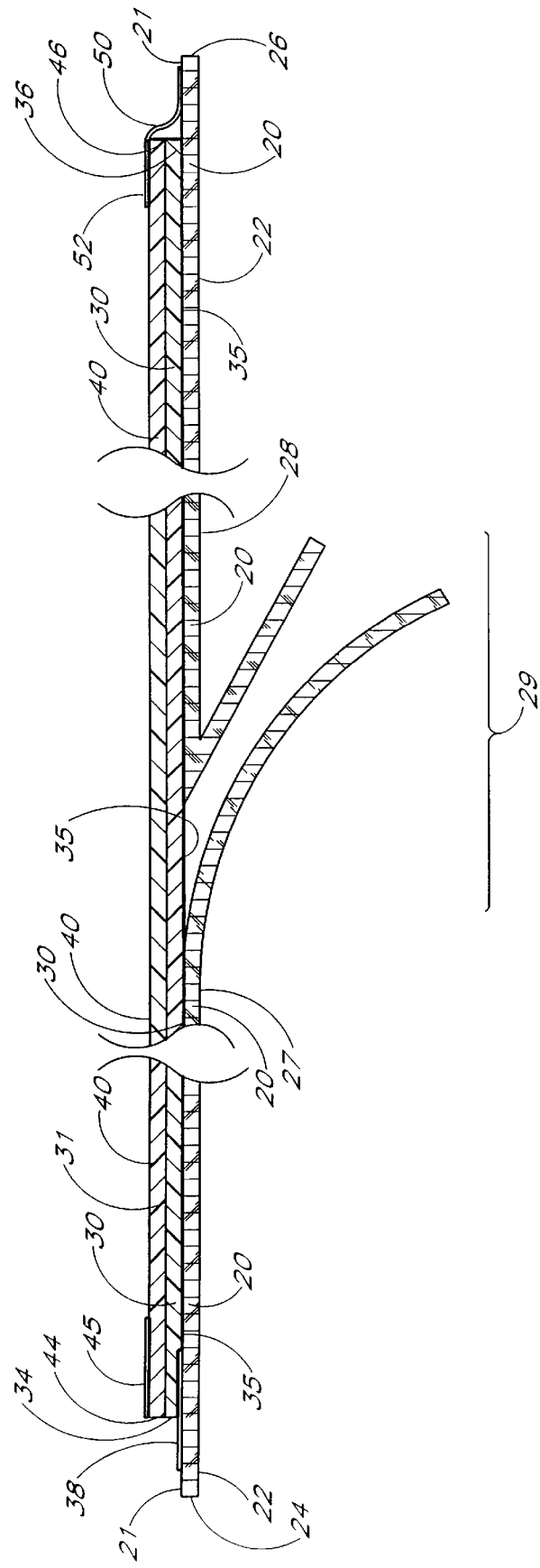
FIG. 2 is a longitudinal cross-sectional view across the combined wound care dressing system of FIG. 1.

Referring to FIGS. 1 and 2, there is depicted a wound care dressing delivery system 10 of the present invention.

Although illustrated in the context of a square wound care dressing, it is to be understood that the inventive features of dressing system 10 may be easily adapted to wound care dressings of a variety of different geometric shapes, such as rectangular and oval shapes. Furthermore, it should be understood the drawings corresponding to the descriptions presented herein are shown with exaggerated thickness and are not to scale, and are thus not meant to imply any dimensional limitations on the elements of the present invention.

Referring to FIG. 1, there is depicted an exploded perspective view of one embodiment of the wound care dressing delivery system of the present invention. Dressing delivery system 10 generally comprises a three-layered sheet, wherein the layers are releasable from one another by varying cohesive forces.

As depicted in FIGS. 1 and 2, the lowest layer is a release layer 20. Release layer 20 has a first surface 21 and second surface 22. Release layer 20 also has a first lateral edge 24 and a second lateral edge 26. Release layer 20 is divided into a first portion 27 and a second portion 28 by a cut 29 extending through the release layer. In the preferred embodiment, cut 29 is a butterfly cut with hanging nonadherent portions which advantageously serve as nonadherent grasping points during dressing applications.

Release layer 20 provides a backing for the adhesive wound dressing of the present invention. Consequently, surface 21 of release layer 20 is preferably coated with silicone, to facilitate easy removal of the adhesive wound dressing from release layer 20. Release layers of this type are well known, and typically comprise a paper material which has been coated with silicone on at least one side. Alternatively, other substrates, such polyesters, polyethylene, polypropylene and polyurethane, which likewise can be coated with silicone and function as a release layer, may be incorporated into the present invention. Furthermore, fluorosilicone release agents may be used with these materials as an alternative to silicone.

Referring to FIGS. 1 and 2, the wound dressing comprises an adhesive layer 30 that is adhered to the silicone-treated surface 21 of release layer 20. It is adhesive layer 30 which functions as the wound dressing when applied. Adhesive layer 30 has a first surface 31 which is nonadherent and a second surface 35 which is coated adhesive substance. Preferably, the adhesive substance is uniformly distributed on surface 35, but this is not required. Adhesive layer 30 also has a first lateral edge 34 and a second lateral edge 36. While lateral edges 34 and 36 of adhesive layer 30 may coterminate with lateral edges 24 and 26 of release layer 20 in some embodiments, in one preferred embodiment, edges 34 and 36 terminate prior to edges 24 and 26, such that portions of the surface 21 of release layer 20 are exposed at the ends of the release layer 20.

Adhesive layer 30 is preferably formed of a polyurethane material, having a thickness of approximately 0.001 inches. Other materials suitable for construction of adhesive layer 30 may also be used, such as polymeric materials of copolyesters, ethyl vinyl acetates, polyether block amides, polyethylene, nylon, and ethylene methacrylic acid.

A modified acrylic pressure sensitive adhesive is preferably used as the adhesive substance on surface 35 of layer 30. Alternately, other pressure sensitive adhesives known to those of skill in the art to adhere to both silicone treated release layers and safely to the skin of a patient may also be used. For example, alternate adhesive materials include acrylic adhesives, rubber based adhesives, silicone based adhesives, modified acrylic based adhesives, water activated adhesives (hydroactive), hydrophobic adhesives, hydrophilic adhesives, pressure sensitive adhesives. In some instances, nonpressure sensitive adhesives having the appropriate adhesive properties may also be used. Additional suitable adhesives are disclosed in U.S. Pat. No. 5,415,627 to Rasmussen et al., the entirety of which is incorporated herein by reference.

A handling strip 38 may be adhered to adhesive surface 35 along the region adjacent lateral edge 34. Strip 38 is nonadherent on both sides, such that when it is adhered to surface 35, it creates a nonadherent region which permits the clinician to handle and place layer 30. In one preferred embodiment, strip 38 is formed of a polyester material, such as Mylar (TM), and is from about 0.001 inches to about 0.003 inches in thickness. Other types of polymeric materials, such as polyvinyl chlorides, polyethylene, polypropylene, and the like, may also be used to form strip 38. Nonpolymeric materials with sufficient flexibility, such as Kraft paper, are also suitable to form strip 38. The width of strip 38 may vary considerably, depending upon the size of the wound dressing, but should possess sufficient width so that a clinician may conveniently grasp strip 38 without also touching surface 35. Generally, a strip 38 of about 0.5 inches in width should be sufficient.

A protective layer 40 is disposed over adhesive layer 30 on nonadherent face 31. Protective layer 40 is generally thicker than layer 30, and because of the cohesive interactions between the two layers, layers 30 and 40 adhere to one another during dressing application. This makes the dressing easier to apply, and protects the thin dressing layer 30 from damage during transport and application. Once layer 30 is adhered to the patient, layer 40 can be easily removed, as described below.

Layer 40 is nonadherent on both sides, and is releasably secured to adhesive layer 30 by cohesive static interactions between the nonadherent face 31 of adhesive layer 30 and protective layer 40. In one preferred embodiment, a polyester material, having a thickness of from about 0.001 inches to 0.003 inches is used to form protective layer 40. Other suitable materials for manufacture of protective layer 40 include polypropylene, polyethylene, and kraft paper.

A second strip 45 may be adhered to the surface of protective layer 40. Preferably, strip 45 is adhered to layer 40 on its exposed surface which is the surface opposite that in contact with adhesive layer 30. However, in some embodiments, strip 45 may be adhered to protective layer 40 on the surface in contact with layer 30. Strip 45 functions to identify the terminal edge 34 of layer 40, and may also function to facilitate separation of layer 40 from layer 30. As shown in FIG. 2, strip 45 has a lateral edge which coterminates with the lateral edge 44 of sheet 40. However, in alternate embodiments, strip 45 may overhang protective layer 40, to create a grasping surface to facilitate separation of protective layer 40 from adhesive layer 30. Strip 45 may be formed from a variety of materials, such as kraft paper, polyester, polyethylene, or other suitable polymeric materials. An acrylic or rubber based adhesive may be used to adhere strip 45 to protective layer 40.

Strip 45, when coterminating with layers 30 and 40, provides several important advantages to the present invention. First, because strip 45 is made from a material which is more rigid than that used to form layers 30 or 40, strip 45 facilities separation of layers 30 and 40 when dressing 10 is bent at coterminal edges 34 and 44. That is, the bending action at the edges 34 and 44, combined with the rigidity of strip 45, disrupts the cohesive forces between layers 30 and 40 at the lateral edge, causing layers 30 and 40 to separate at edges 34 and 44. Once separated, the clinician may grasp layer 40 at edge 44 and peel layer 40 from layer 30.

A second important benefit provided by coterminating strip 45 is that it provides a convenient "pause point" for the clinician when layer 30 is peeled from layer 20 from butterfly cut 29 in the direction of edges 34 and 44. As layer 20 is peeled away from layer 30, the weight and bend of the peeled portion of layer 20 hanging down from dressing 10 creates a separation force between the remaining adhered portions of layers 20 and 30. This force tends to increase as more of layer 20 is peeled from layer 30. In the absence of strip 45, this force is normally sufficient to cause layers 20 and 30 to separate completely as the peeled portion nears edges 24 and 34. This is undesirable, as it makes it more difficult for the clinician to place the dressing on the patient without the dressing folding back upon itself, or accidently adhering to the clinician.

However, the rigidity of strip 45 helps to counteract the separation force between layers 20 and 30 as the peeled portion of layer 20 nears edges 24 and 34. As a result, layers 20 and 30 will not separate without the application of an additional peeling force by the clinician. Consequently, strip 45 creates a peeling "pause point" near edges 24 and 34, which advantageously provides the clinician with more control over the application of dressing 10 to a patient.

Referring to FIG. 2, there is shown a longitudinal cross-section of dressing system 10 across the region near lateral edge 26. As shown in FIG. 2, lateral edge 26 terminates at a point beyond that of edges 36 and 46, such that lateral edge 26 extends beyond edges 36 and 46. Thus, a portion of the surface 21 of release layer 20 is exposed at this point.

A hinge strip 50 is adhered along lateral edge 46 of layer 40 and the exposed surface 21 of release layer 20 which extends beyond edges 36 and 46. Strip 50, when attached to layers 20 and 40 in this manner, acts as a hinge. As described below, this helps to create a nonadhesive handling region to adhesive layer 30 without the presence of additional non-adherent strips. This permits for ease of wound dressing application while at the same time simplifying the design to reduce manufacturing costs.

Hinge strip 50 may be made from a variety of different polymeric materials. In one preferred embodiment, hinge strip 50 is formed of Mylar (TM), and has a thickness of from about 0.001 inches to about 0.003 inches. Other embodiments might be made of different polymeric materials, such as polyvinyl chloride, polyethylene, polypropylene, and in some embodiments, nonpolymeric materials, such as kraft paper. An adhesive 52, preferably a silicone based adhesive, is used to bond hinge 50 to layers 20 and 40.

Figure 3:
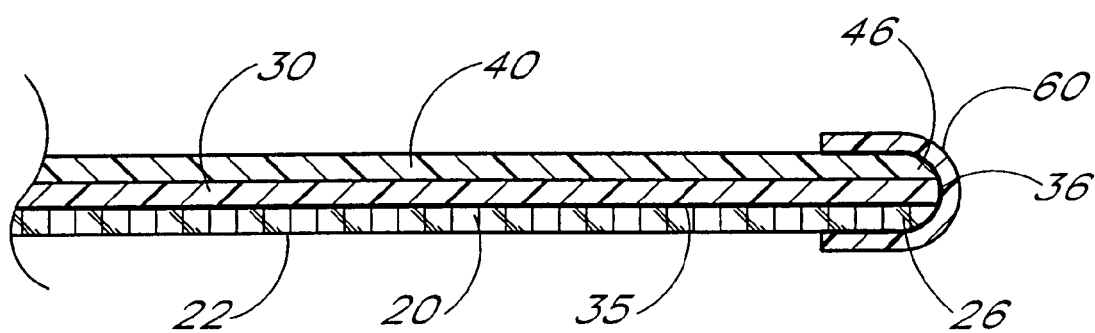
FIG. 3 is a longitudinal cross-sectional view across an alternative embodiment of the hinged end of the wound care dressing system.

Referring to FIG. 3, there is shown an alternative embodiment of the hinge strip used in the present invention. As shown in FIG. 3, lateral edges 26, 36, and 46, all terminate together, such that there is no extending lateral edge 26 as in FIG. 2. In this embodiment, hinge strip 60 is attached to the upper surface of layer 40, and folded around edges 46, 36, and 26, and bonded to surface 22 of layer 20, to form the hinge structure.

The primary features of wound dressing systems 10 which permit ease of application and simplified design resulting in reduced manufacturing cost are the hinge attachment of layers 20 and 40, in combination with the cut in release layer 20. This design has the effect of providing a nonadhesive attachment, similar to the grasping strips of the prior art, to adhesive layer 30 for each of dressing application, without the additional component cost. Moreover, because the design is simpler, it costs less to manufacture.

The improved design of the present invention is best illustrated by description of its method of use. For example, to apply the wound dressing of the present invention from system 10, portion 28 of release layer 20 is peeled back to expose the overlying adhesive surface 35 of layer 30. The exposed portion of layer 30 is then applied to the patient at the site to be treated, until it adheres to the patient. Then, portion 27 of layer 20 is peeled back to expose the overlying adhesive surface 35 while adhesive layer 30 is worked over the patient to dress the wound site. After the dressing has been applied, protective layer 40 may be easily removed from layer 30 by pulling on portion 28. This is because hinge 50 connects layer 40 to portion 28.

Furthermore, because of the improved design of the present invention, a clinician has more flexibility in cutting the wound dressing system while still maintaining ease of application. For example, if sheet 10 were cut through portion 27 along a line parallel to strip 38, the divided sheets would each retain sufficient nonadhesive structure to permit the clinician to easily apply the smaller-sized wound dressing. This is because the portion having strip 38 has an independent nonadherent site for the clinician to grasp, while the portion having the hinge strip 50 and butterfly cut 29 in release layer 20 has sufficient nonadherent structure for application as well.

Figure 4:
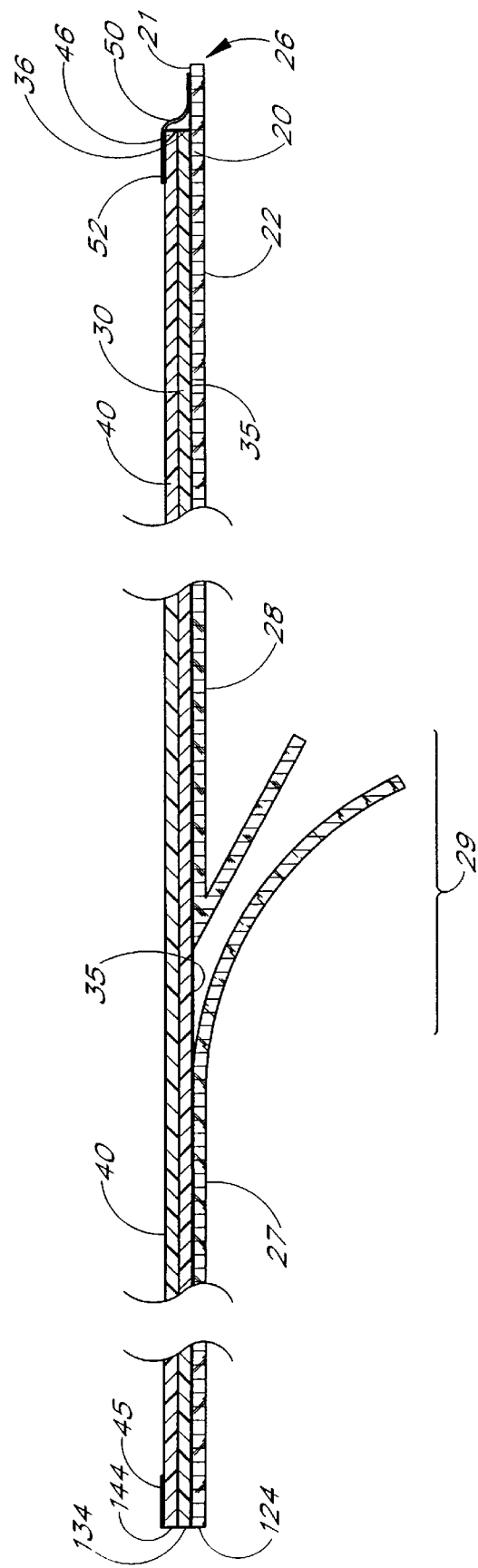
FIG. 4 is a longitudinal cross-sectional view across an alternative embodiment of the present invention.

Because the combination of hinge strip 50 and butterfly cut 29 present a novel nonadherent interface for the clinician to handle the adhesive wound dressing, there is furthermore no need to even provide a strip 38 for grasping on the lateral edge opposite of that of hinge 50. This embodiment is shown in FIGS. 4. As shown in FIG. 4, wound dressing system 100 features layers 20, 30, and 40, cut region 29, and hinge 50, as described above. At lateral edge 110, however, dressing system 100 eliminates the handling strip 38 of the previously described embodiment. As shown in FIG. 4, lateral edge 110 is provided with coterminating edges 124, 134, and 144 of layers 20, 30, and 40, respectfully. Lateral edge 134 of layer 30 is adhered directly to the silicone treated surface of lateral edge 124 of layer 20. Strip 45, described previously, is adhered to the exposed surface of protective layer 40. Because the handling strip 38 need not be provided, dressing system 100 is easier to manufacture and costs less to produce, which in turn, saves both clinical providers and patients money.

In certain applications, it may be desirable to duplicate the nonadherent handling interface created by hinge 50 and cut 29 at opposite lateral edges of the wound dressing system. This embodiment is shown in FIG. 5. As depicted there, the wound dressing system 200 has a hinge structure 50, identical in construction to that described above in connection with FIG. 2, at each of opposite lateral edges 24 and 26. Consequently, wound dressing system 200 is provided with two distinct nonadherent interfaces created by the combination of each hinge 50 with the butterfly cut 29.

Although the present invention and its advantages have been described in detail by referring to specific embodiments, it should be understood that various changes, substitutions and alterations can be made to such embodiments, as is known to those of skill in the art, without departing from the spirit and scope of the invention which is defined by the following claims.

What is claimed is:

1. A wound dressing application system, comprising:
   a release layer having a first lateral edge and a second lateral edge, the layer having a cut extending across the layer to form a first portion and a second portion;
   an adhesive layer releasably adhered directly to an upper surface of the release layer, the adhesive layer having a first lateral edge and a second lateral edge, wherein the second lateral edge of the adhered adhesive layer terminates prior to the second lateral edge of the release layer such that a portion of the release layer upper surface is exposed;
   a protective layer disposed over and contacting a nonadherent surface of the adhesive layer, the protective layer having a first lateral edge and a second lateral edge, wherein the second lateral edge of the protective layer substantially coterminates with the second lateral edge of the adhesive layer; and
   a strip adhered to the protective layer along its second lateral edge and to the exposed upper surface of the release layer, thereby forming a hinge.

2. The wound dressing of claim 1, wherein the cut comprises a butterfly cut in the release liner.

3. The wound dressing application system of claim 2, further comprising a nonadherent strip adhered to the adhesive layer along the first lateral edge of the adhesive layer.

4. The wound dressing application system of claim 2, further comprising a protective layer strip adhered to an upper surface of the protective layer along the first lateral edge of the protective layer.

5. The wound dressing application system of claim 4, wherein the adhesive layer is formed at least in part from polyurethane.

6. The wound dressing application system of claim 5, wherein the adhesive layer is about 0.001 inches thick.

7. The wound dressing application system of claim 5, wherein the protective layer is formed of a polymeric material which is silicone coated, and the protective layer is releasably secured the adhesive layer.

8. The wound dressing application system of claim 7, wherein the release layer is a silicone coated paper substrate.

9. A wound dressing system, comprising:
   a first layer having a cut dividing it into a first portion and a second portion;
   a second layer releasably adhered directly to the first layer, wherein the second layer is adapted to be peeled from the first layer and adhered to a patient;
   a third layer disposed over and contacting the second layer; and
   a strip adhered to the first and third layers to attach the first layer to the third layer.

10. The wound dressing system of claim 9, wherein the first layer is a release layer, the second layer is an adhesive layer, and the third layer is a protective layer.

11. The wound dressing system of claim 10, further comprising a nonadherent strip adhered to an adhesive surface of the adhesive layer to create a nonadherent grasping region on the adhesive layer.

12. The wound dressing system of claim 9, wherein the first layer and third layer have coterminating lateral edges, and the strip is adhered to the first and third layers at the coterminating lateral edges.

13. A method of applying a tacky wound dressing to a patient, comprising the steps of:
   (a) providing a wound dressing system comprising a release layer having a first lateral edge and a second lateral edge, the layer having a cut extending across the layer to form a first portion and a second portion, and an adhesive layer releasably adhered directly to an upper surface of the release layer, the adhesive layer having a first lateral edge and a second lateral edge, wherein the second lateral edge of the adhered adhesive layer terminates prior to the second lateral edge of the release layer such that a portion of the release layer upper surface is exposed, and a protective layer disposed over and contacting a nonadherent surface of the adhesive layer, the protective layer having a first lateral edge and a second lateral edge, wherein the second lateral edge of the protective layer substantially coterminates with the second lateral edge of the adhesive layer, and a strip adhered to the protective layer along its second lateral edge and to the release layer, thereby forming a hinge;
   (b) peeling at least the first or second portion of the release sheet adjacent to the cut away from the adhesive layer to expose an adhesive surface of the adhesive layer;
   (c) applying the adhesive surface of the adhesive layer to a patient to adhere the adhesive layer to the patient; and
   (d) removing the protective sheet from the adhesive layer.

* * * * *